United States Patent [19]

Sih

[11] 4,103,006
[45] Jul. 25, 1978

[54] GLYCOSIDES OF 2,6-BIS(HYDROXY-PHENYL)-3,7-DIOXABICYCLO [3,3,0] OCTANE

[75] Inventor: Charles J. Sih, Madison, Wis.

[73] Assignee: Wisconsin Alumni Research Foundation, Madison, Wis.

[21] Appl. No.: 688,275

[22] Filed: May 20, 1976

[51] Int. Cl.$^2$ .................. A61K 31/70; C07H 15/00
[52] U.S. Cl. .................................. 424/181; 195/49; 260/347.3; 260/347.7; 260/347.8; 424/180; 536/4; 536/120
[58] Field of Search .............. 536/4, 120; 424/180, 424/181

[56] References Cited

U.S. PATENT DOCUMENTS

| | | | |
|---|---|---|---|
| 2,450,086 | 9/1948 | Hales | 536/4 |
| 3,903,071 | 9/1975 | Holmes | 536/4 |

*Primary Examiner*—Johnnie R. Brown
*Attorney, Agent, or Firm*—Howard W. Bremer

[57] ABSTRACT

Mono- and di-glycosides of 2,6-bis (hydroxy-phenyl)-3,7-dioxabicyclo [3,3,0] octane and methods for preparing such compounds. The compounds exhibit antihypertensive properties.

25 Claims, No Drawings

GLYCOSIDES OF 2,6-BIS(HYDROXY-PHENYL)-3,7-DIOXABICYCLO [3,3,0] OCTANE

The invention described herein was made in the course of work under a grant or award from the Department of Health, Education, and Welfare.

This invention relates to compounds which exhibit anti-hypertensive properties.

More specifically, this invention relates to compounds which are the glycosides of 2,6-bis(hydroxyphenyl)-3,7-dioxabicyclo [3, 3, 0] octane.

It has long been known that tea or wine made from Tu Chung (Eucommia ulmoides Oliver) exhibited hypotensive effects. (See, for example, Pharmacological Action of Eucommia Ulmoides, Oliv., Jap. J. Pharmacol, 6, 122–137 (1957) and The Mechanism of the Hypotensive Action of Tu Chung (Eucommia ultmoides Oliver), Far East Med. J., Vol. 6, September, 1970. The latter publication concludes that the hypotensive action of Tu Chung extract appears to be predominantly peripheral.

The studies which the above-referenced papers report were conducted with crude extracts of Tu Chung and no adducement was made as to whether one or multiple active principles were present in the extract to which the hypotensive effects exhibited could be attributed. Nor was any active principle either isolated or identified.

It has now been found that certain pinoresinol glycosides are effective anti-hypertensive agents.

One of this class of compounds has been isolated from Tu Chung and has been identified as the major active anti-hypertensive principle in Tu Chung. The isolation and identification was established in accordance with the following Example.

EXAMPLE 1

*Eucommia ulmoides* oliv. bark (4.75 kg) was ground into a powder and extracted continuously with 52 liters of acetone, which upon evaporation gave 318 g of residue. The remaining bark was further extracted continuously with 52 liters of 95% ethanol, which upon evaporation afforded 274 g of residue. The ethanol extract residue was dissolved in 1370 ml of distilled water and centrifuged at 2000 × G for 10 minutes. The supernatant was decanted and evaporated to yield 180 g of an oily residue, which was chromatographed over a silica gel (MN-Kieselgel, Brinkmann) column (72.5 × 9.6 cm). The column was eluted with $CHCl_3:CH_3OH:H_2O$ (5:4:1) and 500 ml fractions were collected. [Fractions 5-8 (29.15 g); 9-14 (53.23 g) and 15-19 (16.91 g)]. Fraction 9-14 (53 g) was chromatographed on another silica gel (MN) column (72 × 9.6 cm) and was eluted with $CHCl_3:CH_3OH:H_2O$ (65:35:10 using the organic layer); 15 ml fractions were collected. [Fractions 269-1227 (24.32 g); fractions 1228-1539 (5.6 g)]. Fractions 1228-1539 (5.6 g) was chromatographed on another silica gel (MN) column (5.6 × 70 cm) and the column was eluted with $CHCl_3:CH_3OH:H_2O$ (65:25:10, using the organic layer) and again 15 ml fractions were collected. [Fractions 191-540 (1.2 g); 541-810 (3.08 g); 811-890 (0,321 g)]. Fraction 541-810 (3.08 g) was chromatographed again on a silica gel (MN) column (5.6 × 58 cm) and the column was eluted with $CHCl_3:CH_3OH:H_2O$ (65:25:10, organic layer), and 15 ml fractions were collected. Fractions 473-627 were pooled and evaporated to yield 2.2 g of crude pinoresinol diglucoside, which upon three recrystallizations from 70% ethanol gave an analytical sample (1.2 g), m.p. 221°–230° C; $[\alpha]_D^{25}$ −27.3° (c, 0.54, $H_2O$); uv ($H_2O$) 276 nm ($\epsilon$ 6,750), 226 ($\epsilon$ 21,500); IR (KBr) 3420, 2880, 1600, 1520, 1425, 1276, 1232, 1082, 1054, 1040, 902, 818 cm$^{-1}$. Anal. Calcd. for $C_{32}H_{42}O_{16}$. $4H_2O$: C, 50.92; H, 6.68. Found: C. 51.23; H. 6.70.

It was determined from the foregoing physico-chemical data that the isolated compound was a pinoresinol glucoside (the diglucoside of 2,6-bis (4-hydroxy-3 methoxyphenyl)-3,7-dioxabicyclo [3, 3, 0] octane) consisting of (±)-pinoresinol linked to two D-glucose residues via β-glucosidic bonds and has the following formula:

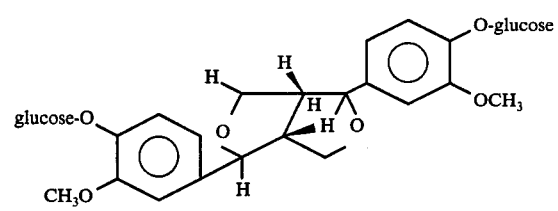

which is more conveniently depicted for purposes of this application as follows:

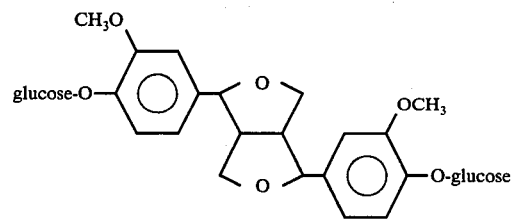

The anti-hypertensive activity of this compound was measured according to the procedure described by F. R. Domer in "Animal Experiments in Pharmacological Analysis", Charles C. Thomas, publisher, Springfield, Ill. (1971) p. 61, except that the sample to be tested for antihypertensive activity was introduced through the jugular vein of spontaneous hypertensive rats (SHR). The SHR rats (170–260 g; 9–10 weeks old) of the Okamoto-Aobi strain were obtained from Raconic Farms, Inc., Germantown, N.Y. The results obtained are shown in the table below.

Table 1

| Compound | Dose | Decrease in diastolic blood pressure (mm) |
|---|---|---|
| Natural pinoresinol diglucoside | 30 mg/kg | 25, 35* |
| | 40 mg/kg | 80 |
| | 100 mg/kg | 105, 90, 110, 120 |

*each value given represents a single rat

In general, the compounds of this invention have the formula

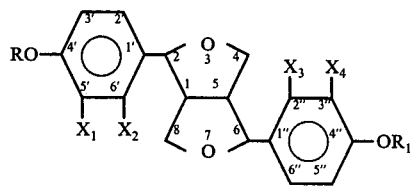

where R and $R_1$ are each selected from the group consisting of hydrogen, a monosaccharide and a disaccharide, with at least one of R and $R_1$ being a monosaccharide or disaccharide, and $X_1$, $X_2$, $X_3$ and $X_4$ are each selected from the group consisting of hydrogen, lower alkyl, chlorine, amino and $OR_2$ where $R_2$ is hydrogen or lower alkyl.

It will be understood that since the structure of the compounds of this invention as shown above, is wholly symmetrical the positions of $X_1$ and $X_2$ and $X_3$ and $X_4$ on the phenyl groupings as depicted is not to be considered limiting. Thus, instead of attachment at the 2', 3' and 2", 3" positions as shown they could as well be at the 2', 3' and 5", 6" positions. It is essential, however, that the O-glycoside be in the para-position on the phenyl ring with respect to the attachment postion of that ring to the dioxabicyclo nucleus of the compound.

It is also to be understood that the compounds of this invention as described above are to be considered to include stereoisomers of pinoresinol at the 2 and 6 positions in the molecule.

Broadly speaking, the compounds of this invention may be termed glycosides of 2,6-diacy-3,7-dioxabicyclo [3, 3, 0] octanes.

Examples of mono- and disaccharides which find ready application as R and $R_1$ in the structure shown above are various aldohexoses, such as, galactose mannose and glucose, ketohexoses, such as fructose, aldopentoses such as xylose, arabinose and ribose, and the disaccharides maltose and lactose. $X_1$, $X_2$, $X_3$ and $X_4$ can, in addition to hydrogen, be lower alkyl, such as methyl, ethyl, propyl and butyl or hydroxyl, or oxyalkyl, such as methoxy, ethoxy, propoxy and butoxy, or halogen, or amino. Nor do all of $X_1$, $X_2$, $X_3$ and $X_4$ have to be the same substituent group. Within the reasonable limits of synthesis each of $X_1$, $X_2$, $X_3$ and $X_4$ may be a different group or any admixture of any of the groups above named.

The preferred compounds of this invention are the glycosides of 2,6-bis(4-hyroxy-3-methoxy phenyl)-3,7 -dioxabicyclo [3, 3, 0] octane.

The compounds of this invention may be administered as sterile parenteral solutions by injection or intravenously or by alimentary canal in the form of oral dosages, or by suppository. Doses of from about 20 to 100 mg/kg are effective amounts for practicing this invention with a projection of about 8-10 mg doses on a daily basis as maintenance dosages.

Dosage form of the compounds can be prepared by combining them with a non-toxic pharmaceutically acceptable carrier as is well known in the art. Such carriers may be either solid or liquid such as, for example, corn starch, lactose, sucrose, peanut oil, olive oil, sesame oil and water. If a solid carrier is used the dosage forms of the compounds of the invention may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

It should be understood that although dosage ranges are given, the dose range of any particular compound to be administered to a host will depend upon the specific anti-hypertensive activity of the compound employed. Other factors, well known to those skilled in the art in the therapeutic use of medicinal agents, must also be taken into account in establishing dosage levels. Obviously, the particular compound chosen for a particular dosage form must be present in such form in a unit amount sufficient to exert an anti-hypertensive effect.

As will be evident from the following Examples, the primary material utilized in preparing the compounds of this invention is (±) pinoresinol. Although several methods preparing this compound have been reported in the literature (See, for example, R. J. Anderegg and J. W. Rowe, Holzforschung Bd. 28 (1974) H 5, p. 171; K. Kratzl and G. E. Miksche Monatsch 94, 434 (1963) and K. Freundenberg & H. Dietrich, Chem. Ber 86, 1157 (1953).) the yields of (±) pinoresinol were inadequate to the requirements for pharmocological evaluations.

It has now been found that (±) pinoresinol can be prepared biochemically from coniferyl alcohol in excellent yield through the use of chloroperoxidase elaborating microorganism in accordance with the following general sequence:

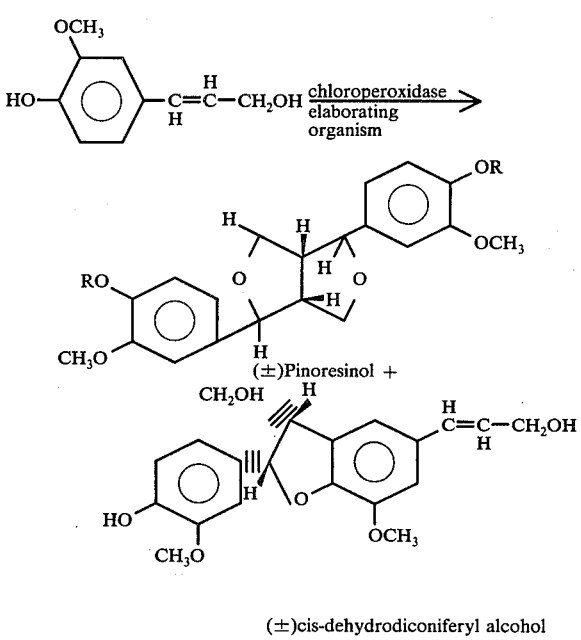

The preferred chloroperoxidase elaborating microorganism for this biochemical synthesis is *Caldariomyces fumago* ATCC 16373 and the synthesis can be accomplished in several ways as outlined below.

Biochemical Synthesis of (±)-Pinoresinol

Method A

Growing Culture

The surface growth from a one week old agar slant of *Caldariomyces fumago* ATCC 16373 was suspended in 5 ml of saline (0.85%) solution. Two ml portions of this suspension were used in inoculate 50 ml of the soybean-dextrose medium (soybean meal 5 g; dextrose 20 g; NaCl 5 g; $K_2HPO_4$ 5 g; yeast extract 5 g; water 1 liter; pH adjusted to 7.0; autoclaved at 15 psi for 15 minutes, held in a 250 ml Erlenmeyer flask (F-1 stage). The flasks were incubated at 25° C on a rotary shaker (250 cycles/min-2 inch radius) for 72 hours, after which a 10% by volume transfer was made to each of three 2-liter Erlenmeyer flasks (F-2 stage), containing 500 ml of the soybean dextrose medium. After 48 hours of incubation on a rotary shaker, 2.5 g of coniferyl alcohol, dissolved in 4 ml of Dimethyl formamide was added to each flask.

The F-2 stage flasks were then incubated for an additional 16 hours under the conditions used in the incubation of the F-1 stage flasks.

Isolation

Sixteen hours after the addition of the coniferyl alcohol, the cells were removed by centrifugation. The combined supernatant (1.4 liters) was cooled and carefully adjusted to pH 2.5 with 2N acetic acid, and was exhaustively extracted with 1 liter of ethyl acetate three times. The combined ethyl acetate layer was dried over $Na_2SO_4$ and evaporated to afford an oily residue. The oily residue (8.2 g) was chromatographed over a silica gel (Brinkman) column (30 × 2.2 cm). The column waas eluted with a gradient system comprised of ethyl acetate-methanol (97:3) to yield 810 mg (±) pinoresinol, m.p. 157–158° C, nmr (CDClhd 3) $\delta^{TMS,}$ 3.1(2H, m), 3.9 (6H, s), 3.85 (2H, m), 4.25 (2H, m), 4.72 (2H, m), 6.88 (6H, m) and 798 mg of cis-dehydro-diconiferyl alcohol, m.p. 160°–161° C; m/e 358 (M+), 340 (M-18), 325 nmr

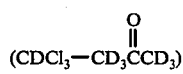

$\delta^{TMS}$ 2.95 (1H, m), 3.6 (2H, m), 3.86 (3H, s), 3.9 (3H, s), 4.2 (2H, m), 5.58 (1H, d), 6.35 (2H, m), 6.9 (5H, m).

Method B

C. fumago ATCC 16373 was grown and a solution of crude chloroperoxidase was prepared in accordance with the methods described in S. L. Neidleman and M. A. Oberc, J. Bacteriol., 95, 2424 (1968); S. L. Neidleman, A. I. Cohen, and L. Dean, Biotech. and Bioeng., 11, 1227(1969).

To 200 ml of this enzyme solution was added 40 ml of 0.3% hydrogen peroxide, 80 ml of 0.3M potassium phosphate buffer (pH 6.0), 200 mg of coniferyl alcohol in 10 ml of dimethyl formamide, and 20 ml of distilled water. After incubation on a rotary shaker (250 cycles per minute, 1 inch in stroke), at 25° C for 20 min, the reaction mixture was carefully acidified to pH 2.0 and exhaustively extracted with ethyl acetate. The ethyl acetate extract was dried with anhydrous sodium sulfate and was concentrated at reduced pressure to dryness. Chromatography of the residue on a silica-gel column as described in Method A above gave 25 mg of (±)-pinoresinol, m.p. 157°–158° C and 30 mg of cis dehydrodiconiferyl alcohol.

Method C

C. fumago ATCC 16373 was grown and a chloroperoxidase-containing culture filtrate was prepared as described by D. R. Morris and L. P. Hager, J. Biol. Chem., 241, 1763 (1966). (During growth chloroperoxidase is liberated into the culture medium and therefore the cell-free medium (culture filtrate) can be used for the coupling of coniferyl alcohol.)

To 50 ml of the chloroperoxidase-containing culture filtrate was added 10 ml of 0.3% hydrogen peroxide, and the pH of the incubation mixture was adjusted to 5.0 with acid. 50 mg of coniferyl alcohol in 2 ml of dimethylformamide was then added to the pH adjusted mixture. After incubation at 25° C for 20 min, the pH was adjusted to 2.5 and extracted with ethyl acetate three times. Application of the same isolation procedure as described in Method A gave 6 mg of (±)-pinoresinol and 7 mg of cis-dehydrodiconiferyl alcohol.

In the foregoing Methods the coniferyl alcohol can be prepared as follows:

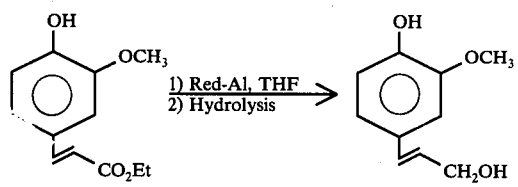

Ethyl ferulate, 1.04 g (0.00466 mol), was dissolved in 10 ml of dry THF to produce a clear pale yellow solution. This solution was added to a 100 ml round bottom flask that previously was dried and flushed with dry $N_2$. The solution was rapidly stirred and 5.65 g (0.028 mol, 6 molar eq) of sodium bix(2-methoxyethoxy) aluminum hydride (Red-Al) was added dropwise so as to prevent too vigorous a reaction. The reaction mixture was stirred for 1 hour after all the reducing agent was added. Next, the reaction was chilled to 0° C and 30 ml of a saturated aqueous solution of sodium tartarate was added (with caution). The homogeneous pale yellow reaction mixture was extracted with 3 × 50 ml ether. The ether was dried and evaporated to yield 957.8 mg of a pale yellow oil, which, upon column chromatography (Silica gel, $CHCl_3$), produced 353 mg (42%) of coniferyl alcohol (mp = 74°–75° C; $CHCl_3$).

Alternatively, coniferyl alcohol can be prepared by mercuric acetate oxidation of eugenol under the conditions reported by Z. Rappaport, J. Winstein, and W. G. Young, J. Am. Chem. Soc, 94, 2320 (1972) as follows.

A mixture of eugenol acetate (16 g, 0.0777 mol) and mercuric acetate (44.5 g, 1.4 mol) in 160 ml of acetic acid was refluxed for 20 hr. After filtration, the acetic acid solution was poured into water (150 ml) and extracted with ether (200 ml). The etheral solution was washed successively with water, aqueous $NaHCO_3$, saturated NaCl solution and dried ($Na_2SO_4$). The solvent was evaporated to give 18 g of coniferyl acetate. Subsequent reduction of the coniferyl acetate with Red-Al gave coniferyl alcohol.

Synthesis of compounds of this invention can be readily accomplished utilizing the general procedure of K. Freudenberg and H. H. Hubner, Chem. Ber. 85, 1181 (1952) for the preparation of hydroxy cinnamyl alcohols with the exception of the reduction step. In the process of this invention, the general schematic for which is set forth below, the reduction is carried out using "Red-Al" (bis(2-methoxyethoxy)-aluminum hydride).

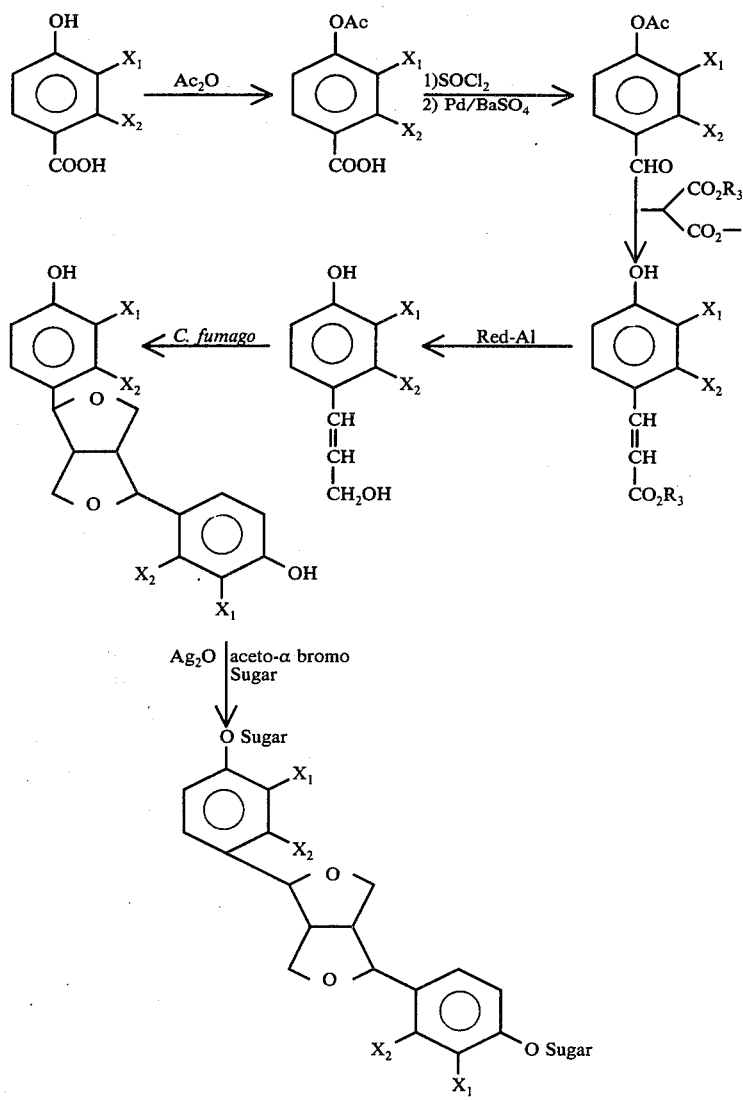

In the foregoing schematic sequence $R_3$ can be a lower alkyl such as methyl, ethyl, propyl or butyl and $X_1$ and $X_2$ can each be selected from the group consisting of hydrogen, lower alkyl, chlorine, amino and $OR_2$ where $R_2$ is hydrogen or lower alkyl.

Also, the aceto-bromo sugar reactant shown is to be construed broadly as representative of acetylated glycosyl halides, which are well known reactants in the sugar chemistry art, and the sugar designation is meant to include both monosaccharides and disaccharides. For example, "aceto-α bromo glucose", as used in this application and in the specific Examples means tetra-O-acetyl-α-D-glucopyranosyl bromide. Such other acetylated glycosyl halide reactants as are shown will be correspondingly identified by the particular sugar and halide involved. Thus, when maltose (a disaccharide) is the sugar, the reactant can be identified as aceto-αbromo maltose, or, more specifically, as octa-O-acetyl-α-D-maltopyranosyl bromide. The corresponding aceto-α chloro sugars are also usable for the reactions shown but, in general, the bromo compounds are preferred.

It is to be understood that in the foregoing reaction sequence the microorganism causes dimerization of the coniferyl alcohol and as a consequence the substituents identified by $X_1$ and $X_2$ will be the same in the symmetrical (±) pinoresinol product and in the ultimate pinoresinol diglycoside product. It is also to be appreciated that the reaction of the (±) pinoresinol product with aceto-α bromo sugar in the presence of $Ag_2O$, followed by alkaline hydrolysis, affords the pinoresinol diglycoside product as a mixture of α, β-anomers.

Instead of a dimerization reaction, as shown in the foregoing schematic sequence, C. fumago can also cause a coupling reaction to take place between two differently substituted coniferyl alcohol products. Through the application of such reaction a different mix of substituents in the ultimate pinoresinol diglycoside product can be obtained as shown in the schematic below.

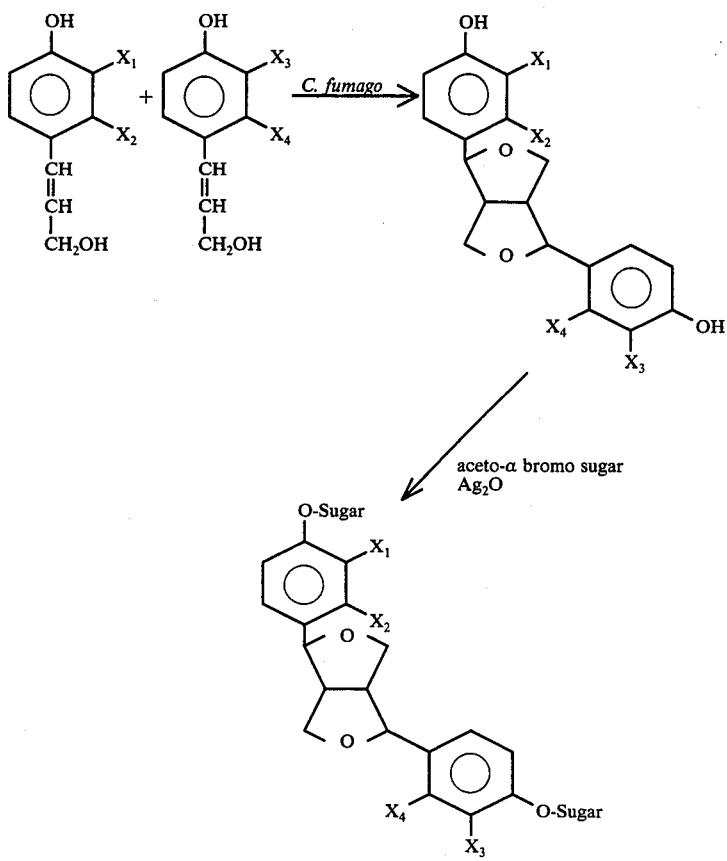

In the above schematic $X_1$, $X_2$, $X_3$ and $X_4$ can each be selected from the group consisting of hydrogen, lower alkyl, chlorine, amino and $OR_2$ where $R_2$ is hydrogen or lower alkyl. Also, the sugar designated in the aceto-α bromo sugar reactant and in the pinoresinol diglycoside product can be a mono- or disaccharide as previously described.

Starting materials for the Freudenberg and Hubner general procedure (referenced supra) are readily available or conveniently prepared. For example, 3-chloro-4-hydroxy benzoic acid and 4-hydroxy-3-nitro-benzaldehyde (useful when the amino group is to be a substituent in the coniferyl alcohol product) can be obtained from Aldrich Chem. Co. of Milwaukee, Wis. while 3-hydroxy-4-methylbenzaldehyde is readily prepared by the method of P. Amakosu and K. Sato, Bull. Chem. Soc. (Japan) 40, 1428 (1967). Other convenient starting material for the synthesis, depending upon the substituents desired in the molecule, will be readily evident to those skilled in the art.

In addition, the chemical synthesis of Kratze and Miksche and Freudenberg and Dietrich referred to above can be used to obtain compounds of this invention, particularly when it is desired that the substituents designated by $X_1$, $X_2$, $X_3$ and $X_4$ are all intended to be different. In utilizing these procedures, however, yields are sacrificed.

In the preceding schematic sequences the ultimate product has been shown in all cases as a di-glycoside of a pinoresinol product. The mono-glycoside can also readily be made utilizing the methods of the present invention as will be evident from the following Examples.

The following Examples illustrate the preparation of various glycosides of this invention but are intended to be illustrative only and are not to be construed as limiting the scope of the invention as set forth in the appended claims.

EXAMPLE 2

Pinoresinol-diglucoside - Silver oxide (2.24 g, 9.65 mmol) was added to a stirred reaction mixture of pinoresinol (358 mg, 1 mmol) and aceto-α bromo glucose (2.24 g, 5.45 mmol) in 6 ml of dry quinoline over a period of 15 min. After stirring the reaction mixture for 16 hours at 25° C, the reaction mixture was extracted with 20 ml of ether. The organic ethereal layer was successively washed with water (2 × 10 ml), 1 N HCl (5 × 5 ml), dilute $NaHCO_3$ (3 × 5 ml) and dried over $Na_2SO_4$. After evaporation of the organic solvent in vacuo, the residue was dissolved in 20 ml of methanol containing 1 ml of 5 N NaOH and the mixture was stirred for 2 hours at 0° C. After acidification to pH 4.5 with 2N HCl, this mixture was evaporated to dryness. The residue was dissolved in 5 ml of water and chromatographed over an Amberlite XAD-2 column (1.9 × 38 cm). The column was washed with 150 ml of water to remove salts. The diglucoside was then eluted off the column with 250 ml of 20% aqueous acetone. The combined acetone fractions were evaporated to dryness and the residue was chromatographed over a silica-gel column (3.5 × 44 cm). Elution of the column with solvent system, $CHCl_3:CH_3OH:H_2O$ (65:30:10) gave 230 mg (34%) of pure pinoresinol diglucoside, m.p. 238–250°; uv ($H_2O$) 276 nm (ϵ6,600) and 226 (ϵ21,900); $[\alpha]_D^{25}$ −15.3° (c, 0.4, $H_2O$); IR (KBr) 1600, 1515, 1414, 1275, 1260, 1230, 1080, 1050, 1030, 993 810 cm$^{-1}$. Anal calcd for $C_{32}H_{42}O_{16}\cdot 4H_2O$: C, 50.92; H, 6.68. Found: C, 50.70; H, 6.70.

Anti-hypertensive activity of this compound was measured in accordance with the procedure of F. R. Domer referred to above utilizing the indicated strain of SHR rats with the following results.

Table 2

| Compound | Dose | Decrase in diastolic blood pressure (mm) |
| --- | --- | --- |
| Synthetic pinoresinal diglucoside | 30 mg/kg | 50 |
| | 90 mg/kg | 120 |
| | 100 mg/kg (separate rat) | 90 |

EXAMPLE 3

Pinoresinol-digalactoside - To a stirred solution of pinoresinol (358 mg, 1 mmol) and aceto-α bromo galactose (Sigma) (2.24 g, 5.54 mmol) in 6 ml of dry quinoline was added 2.24 g (9.65 mmol) of $Ag_2O$ over a period of 15 minutes. After stirring for 18 hours at 25° C, the reaction mixture was extracted with 20 ml of ether. The ethereal layer was successively washed with water, 1 N HCl (5 × 5 ml), dilute $NaHCO_3$ solution and dried over $Na_2SO_4$. After evaporation of the organic solvent, the residue was dissolved in 20 ml of methanol containing 1 ml of 5N NaOH. The reaction mixture was stirred for 2 hours at 0° C and was then acidified to pH 4.5 with 2 N HCl. After evaporation of the solvent, the residue was dissolved in 5 ml of water and chromatographed over an Amberlite XAD-2 column (1.9 × 34 cm). The column was washed with 200 ml of water to remove salts. The desired digalactoside was eluted off the column with 200 ml of 50% aqueous acetone. The combined acetone fractions were evaporated to dryness and the residue was further chromatographed over a silica gel column (4.2 × 41 cm). Elution of the column with $CHCl_3:CH_3OH:H_2O$ (65:25:10) gave 80 mg of pinoresinol digalactoside, m.p. 143°–148°; IR (KBr) 1597, 1510, 1414, 1139, 1262, 1142, 1078, 1050, 1030, 897, 813, 770 cm$^{-1}$; uv ($H_2O$) 276 nm (ε6,580), 226 (ε20,820); $[\alpha]_D^{25}$ +4.5° (c, 0.31, $H_2O$). Anal. calcd for $C_{32}H_{42}O_{16}\cdot 4H_2O$: C, 50.92; H, 6.68. Found: C, 50.78; H, 6.73.

The anti-hypertensive activity was measured in accordance with procedure referred to in the previous Examples utilizing the same strain of SHR rats with the following results:

Table 3

| Compound | Dose | Decrase in diastolic blood pressure (mm) |
| --- | --- | --- |
| Synthetic pinoresinol galactoside | 35 mg/kg | 30 |

EXAMPLE 4

Pinoresinol-dimaltoside - To a stirred reaction mixture of pinoresinol (358 mg, 1 mmol) and aceto-α bromo maltose (Sigma) (3.8 g, 5.43 mmol) in 6 ml of dry quinoline was added 2.24 g (9.65 mmol) of $Ag_2O$ over a period of 15 min. The reaction mixture was stirred at room temperature overnight. Ether (20 ml) was then added and again stirred well and filtered. The organic ethereal layer was washed with water (2 × 10 ml), 1 N HCl (5 × 5 ml), and saturated $NaHCO_3$ solution (2 × 5 ml), dried ($Na_2SO_4$) and evaporated to dryness in vacuo. The residue was dissolved in 20 ml of $CH_3OH$ and the methanolic solution was treated with 5 N NaOH solution (1 ml) at 0° C for 2 hr. After evaporation of the solvent, the residue was chromatographed over an Amberlite-XAD-2 (40 g) column. The column was washed with water (150 ml) and the glycoside was then eluted with 50% aqueous acetone (250 ml). The acetone solutions were combined and evaporated to dryness. The residue was again chromatographed over a silica-gel column (4.7 × 40 cm). Elution of the column with the solvent system, $CHCl_3:CH_3OH:H_2O$ (65:35:10) gave 80 mg (8%) of pure dimaltoside, m.p. 169°–185°. $[\alpha]_D^{25}$ +56.7° (c, 0.43, $H_2O$). uv ($H_2O$) 276 nm (ε7,200), 226 (ε19,800); IR (KBr) 1598, 1513, 1465, 1452, 1420, 1270, 1225, 1140, 1070, 1050, 915, 853, 810, 780 cm$^{-1}$. Anal. calcd for $C_{44}H_{62}O_{26}\cdot 4H_2O$: C, 48.98; H, 6.54. Found: C, 49.14; H, 6.62.

The anti-hypertensive activity of the recovered compound as measured by the same criteria applied in the foregoing Examples was as follows:

Table 4

| Compound | Dose | Decrease in diastolic blood pressure (mm) |
| --- | --- | --- |
| Synthetic pinoresinol dimaltoside | ~ 20 mg/kg | 10 – 20 |

EXAMPLE 5

Pinoresinol-monoglucoside - To a solution of pinoresinol (358 mg, 1 mmol) in 10 ml of chloroform was added acetic anhydride (201 mg, 1.5 mmol) and 0.02 ml of pyridine. The reaction mixture was stirred for 18 hr at room temperature. The organic solution was washed successively with water, 2 N HCl, and saturated $NaHCO_3$ solution. After drying of the chloroform solution ($MgSO_4$), the solvent was evaporated to give 425 mg of crude product in a ratio 1:1.3, corresponded to mono- and di-acetylated pinoresinol according to the estimation. The crude product was used to prepare the monoglucoside without further purification.

To a stirred solution of the crude product (425 mg) and aceto-α bromo glucose (750 mg, 1.83 mmol) in 4 ml of quinoline was added $Ag_2O$ (725 mg, 3.13 mmol) over a period of 15 min. The reaction mixture was stirred for 20 hr at room temperature. Twenty ml of ether was added and the reaction mixture stirred well and filtered. The organic solution was washed successively with water, 1 N HCl, and saturated $NaHCO_3$ solution and dried ($Na_2SO_4$). After evaporation of the solvent, the residue was dissolved in 15 ml of $CH_3OH$ and treated with 0.5 ml of 5 N NaOH for 1 hr at 0° C. The residue obtained on evaporation of the methanol was dissolved in 5 ml of water. The aqueous solution was acidified to pH ~ 4.5 with 1 N HCl at 0° C. The crude product was chromatographed over an Amberite XAD-2 resin (50 g, Rohm & Haas) column. The column was eluted with water (200 ml) followed by 50% aqueous acetone (200 ml). The acetone solutions were combined and evaporated to dryness. The residue was chromatographed over a silica gel column (3.5 × 42 cm). The column was eluted with chloroform-methanol-water (65:20:10) and 14 ml fractions were collected. Fractions 53–65 were combined to yield 92 mg of monoglucoside, mp 125°–140° C; uv max 278 nm (ε6230), 225 (16130); $[\alpha]_D^{25}$ +7.5(C = 0.3 water); ir (KBr) 1650, 1274, 1228, 1078, 1050 cm$^{-1}$; nmr ($D_2O$)$\delta^{DSS}$ 2.93 (2H, m), 3.58 (4H, m), 3.78 (6H, s, b), 4.05 (2H, m) 4.74–4.82 (6H), 4.98

(1H, m), 6,89 (6H, m). Anal. calcd. for $C_{26}H_{32}O_{11}\cdot 2H_2O$: C, 56.11; H, 6.52. Found: C, 56.35; H, 6.28.

The anti-hypertensive activity of the recovered compound as measured by the same criteria applied in the foregoing Examples was as follows:

Table 5

| Compound | Dose | Decrease in diastolic blood pressure (mm) |
|---|---|---|
| Synthetic pinoresinol monoglucoside | 100 mg/kg | 15 – 20 |

Having thus described the invention what is claimed is:

1. Compounds having the formula:

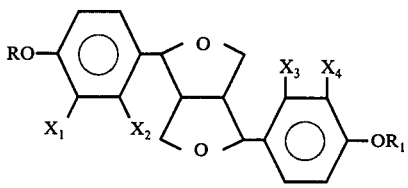

where R and $R_1$ are selected from the group consisting of hydrogen, a monosaccharide and a disaccharide, with at least one of R and $R_1$ being a monosaccharide or disaccharide, and $X_1$, $X_2$, $X_3$ and $X_4$ are each selected from the group consisting of hydrogen, lower alkyl, chlorine, amino and $OR_2$, where $R_2$ is hydrogen or lower alkyl.

2. The compounds of claim 1 which are the glycosides of 2,6-bis [4-hydroxy-3-methoxyphenyl]-3,7-dioxabicyclo [3,3,0] octane.

3. The compounds of claim 1 wherein R and $R_1$ are a monosaccharide, $X_2$ and $X_3$ are hydrogen and $X_1$ and $X_4$ are methoxy.

4. The compounds of claim 3 wherein the monosaccharide is an aldohexose.

5. The compounds of claim 4 wherein the aldohexose is galactose.

6. The compounds of claim 4 wherein the aldohexose is glucose.

7. The compounds of claim 3 wherein the monosaccharide is an aldopentose.

8. The compounds of claim 3 wherein the monosaccharide is a ketohexose.

9. The compounds of claim 8 wherein the ketohexose is fructose.

10. The compounds of claim 1 wherein R and $R_1$ are a monosaccharide and $X_1$, $X_2$, $X_3$ and $X_4$ are hydrogen.

11. The compounds of claim 1 wherein R and $R_1$ are a disaccharide and $X_1$, $X_2$, $X_3$ and $X_4$ are hydrogen.

12. The compounds of claim 1 wherein one of R and $R_1$ is hydrogen and the other is monosaccharide and $X_1$, $X_2$, $X_3$ and $X_4$ are hydrogen.

13. The compounds of claim 1 wherein R and $R_1$ are a disaccharide, $X_2$ and $X_3$ are hydrogen and $X_1$ and $X_4$ are methoxy.

14. The compounds of claim 13 wherein the disaccharide is maltose.

15. The compounds of claim 13 wherein the disaccharide is lactose.

16. The compounds of claim 1 wherein one of R and $R_1$ is hydrogen and the other is a disaccharide and $X_1$, $X_2$, $X_3$ and $X_4$ are hydrogen.

17. An anti-hypertensive composition comprising a pinoresinol glycoside of the formula

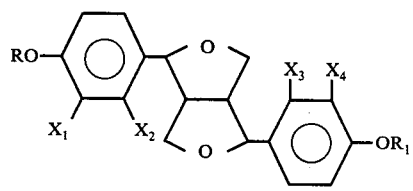

where R and $R_1$ are selected from the group consisting of hydrogen, a monosaccharide and a disaccharide, with at least one of R and $R_1$ being a monosaccharide or disaccharide, and $X_1$, $X_2$, $X_3$ and $X_4$ are each selected from the group consisting of hydrogen, lower alkyl, chlorine, amino and $OR_2$ where $R_2$ is hydrogen or lower alkyl, together with a pharmaceutical excipient.

18. The composition of claim 17 where the pinoresinol glycoside is a glycoside of 2,6bis[4-hydroxy-3-methoxyphenyl]-3,7-dioxabicyclo [3,3,0] octane.

19. The composition of claim 18 wherein the glycoside is pinoresinol diglucoside.

20. The composition of claim 18 wherein the glycoside is pinoresinol monoglucoside.

21. The composition of claim 18 wherein the glycoside is pinoresinol dimaltoside.

22. The composition of claim 18 wherein the glycoside is pinoresinol digalactoside.

23. A method of treating hypertension in a mammal comprising administering to said mammal an effective amount of pinoresinol glycoside of the formula

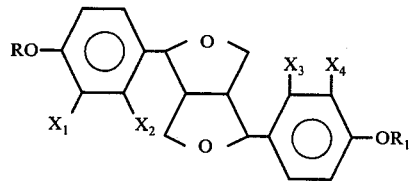

where R and $R_1$ are selected from the group consisting of hydrogen, a monosaccharide and a disaccharide, with at least one of R and $R_1$ being a monosaccharide or disaccharide, and $X_1$, $X_2$, $X_3$ and $X_4$ are each selected from the group consisting of hydrogen, lower alkyl, chlorine, amino and $OR_2$ where $R_2$ is hydrogen or lower alkyl, together with a pharmaceutical excipient.

24. The method of claim 23 wherein the pinoresinol glycoside is a glycoside of 2,6-bis[4-hydroxy-3-methoxyphenyl]-3,7-dioxabicyclo [3,3,0] octane.

25. the method of claim 24 wherein the glycoside is pinoresinol diglucoside.

* * * * *